United States Patent

Bahrmann et al.

[11] Patent Number: 6,054,617
[45] Date of Patent: Apr. 25, 2000

[54] NITRO COMPOUND-REDUCING PROCESS

[75] Inventors: Helmut Bahrmann, Hamminkeln; Boy Cornils, Hofheim; Andreas Dierdorf, Frankfurt; Steffen Haber, Landau, all of Germany

[73] Assignee: Clariant GmbH, Frankfurt, Germany

[21] Appl. No.: 09/011,677

[22] PCT Filed: Aug. 2, 1996

[86] PCT No.: PCT/EP96/03415

§ 371 Date: May 23, 1998

§ 102(e) Date: May 23, 1998

[87] PCT Pub. No.: WO97/07087

PCT Pub. Date: Feb. 27, 1997

[30] Foreign Application Priority Data

Aug. 14, 1995 [DE] Germany ............................ 195 29 874
May 14, 1996 [DE] Germany ............................ 196 19 359

[51] Int. Cl.$^7$ .................................................. C07C 209/32
[52] U.S. Cl. ............................................ 564/416; 564/415
[58] Field of Search .................................. 564/406, 407, 564/415, 416; 568/13, 17

[56] References Cited

U.S. PATENT DOCUMENTS 3,504,035  3/1970  Polinski .
3,944,615  3/1976  Iqbal .
4,157,455  6/1979  Fitton .
4,535,162  8/1985  Mestroni .................................. 546/159
5,057,618  10/1991  Herrmann et al. .
5,087,755  2/1992  Nomura .
5,155,274  10/1992  Herrmann et al. .
5,315,040  5/1994  Kotohiro .................................. 564/422

FOREIGN PATENT DOCUMENTS 0 372 313   6/1990   European Pat. Off. .

OTHER PUBLICATIONS

J.F. Knifton, Homogeneous Catalyzed Reduction of Nitro Coumpounds. IV, Selective and Sequential Hydrogenation of Nitroaromatics, J. Org. Chem., vol. 41, No. 7, 1976, pp. 1200–1205.
P. Khandual et al., Dihydrogen Reduction of Nitroaromatics in Presence of Nickel (II), Palladium (II), and Platinum (II) Acetylacetonates in Homogeneous Phase, J. Indian Chem, Soc., vol. LXIII, Oct. 1986, pp. 901–906.
A. M. Tafesh et al., First Selective Reduction of Aromatic Nitro Compounds Using Water Soluble Catalysts, Tetrahedron Letters, vol. 36, No. 51, pp. 9305–9308, 1995.

*Primary Examiner*—Gary Geist
*Assistant Examiner*—Jean F Vollano
*Attorney, Agent, or Firm*—Scott E. Hanf

[57] ABSTRACT

The invention concerns a process for the reduction of nitro groups to amino groups, characterized that a nitro compound is reacted with hydrogen in the presence of an aqueous solution of a water-soluble metal catalyst of the formula $M(L)_n(Y)_m$ wherein M is ruthenium, rhodium, nickel, or palladium; L, is a water soluble ligand; Y is a further ligand or an alkaline earth ion; n is 1, 2, 3, or 4; and m is 0, 1, or 2.

10 Claims, No Drawings

NITRO COMPOUND-REDUCING PROCESS

This is the national phase of PCT/EP96/03415, filed Aug. 2, 1996.

The invention relates to a process for reducing nitro compounds to give the corresponding amines using a homogeneous palladium, ruthenium, nickel or rhodium catalyst.

The reduction of nitro compounds, especially of nitroaromatics, to give the corresponding amines or anilines has been carried out in industry for over a hundred years. While the reduction by means of iron was still employed industrially until a few years ago, the catalytic reduction using noble metal catalysts on various support materials has recently become established in industry. Although this method has many advantages compared to the reduction by means of iron, problems nevertheless frequently occur in practice. Thus, long filtration times are frequently necessary for separating off the catalyst. The catalysts are usually extremely sensitive to traces of catalyst poisons such as sulfur compounds in low oxidation states, which can lead to the reduction stopping completely. Owing to the nature of a heterogeneous catalyst, the search for the fault if the reaction is unsuccessful is often problematical and sometimes only possible with a considerable outlay in terms of apparatus.

If the nitroaromatic contains halogen substituents, dehalogenation frequently occurs as a secondary reaction. This can be suppressed by selective deactivation of the catalyst, but this makes reproducibility more difficult.

Reductions using homogeneous catalysts which are frequently more efficient compared to heterogeneous catalysts are described, for example, in J. Org. Chem. 1976, 41, 1200 and J. Indian Chem. Soc. 1986, 63, 901. Owing to the problems in separating the catalyst from the product, these reactions have hitherto been carried out only on a laboratory scale. Here too, dehalogenation occurs as a secondary reaction in the case of halogenated nitroaromatics.

It is therefore an object of the invention to provide a process which at least reduces the disadvantages mentioned and makes it possible to reduce nitro compounds to amines in a simple manner and in high yields.

It has now been found that the reduction of nitro compounds with hydrogen in an aqueous system using noble metal catalysis can be carried out under mild conditions and in high yields if the reaction is carried out in the presence of a water-soluble ligand.

EP-A-0 372 313 describes the use of noble metal catalysts having tris(m-sulfophenyl)phosphine as complexing ligand. These catalysts are used in hydrocarbonylations and hydroformylations, particularly in the water gas reaction.

It is therefore surprising that the catalysts mentioned are also suitable for the reduction of nitroaromatics to give the corresponding anilines, without, for example, dehalogenation or C'/C linkage with dehalogenation being observed.

Water-soluble catalysts have hitherto enabled nitroaromatics to be reduced to anilines only when using carbon monoxide or formic acid derivatives (Tetrahedron Letters 1995, 36, 9305). Drawbacks for the industrial implementation of these processes are the acute toxicity of carbon monoxide and the relatively high price of the formic acid derivatives.

The invention accordingly provides a process for reducing nitro groups to amino groups, which comprises reacting a nitro compound with hydrogen in the presence of a water-soluble metal catalyst of the formula (I), $$M(L)_n(Y)_m \qquad (I)$$

where the symbols and indices have the following meanings:
M is ruthenium, rhodium, nickel or palladium;
L are identical or different and are each a water-soluble ligand;
Y are identical or different and are each a further ligand or an alkali metal ion or an alkaline earth metal ion;
n is 1, 2, 3 or 4;
m is 0, 1 or 2.

Nitro compounds are reduced in very high yield and selectivity by means of the process of the invention, and only little dehalogenation occurs in the case of halogenated nitro compounds. The aqueous catalyst solution can be separated off by simple phase separation.

M is preferably rhodium, ruthenium or palladium.

The reaction medium employed is preferably water and the water-soluble catalyst is preferably used in the form of an aqueous solution.

Water-soluble ligands suitable for the process of the invention contain, for example, sulfonate salt groups and/or sulfonic acid groups and/or carboxylate salt groups and/or carboxylic acid groups and/or phosphonate salt groups and/or phosphonic acid groups and/or phosphinate salt groups and/or phosphinic acid groups, and/or phosphonium groups and/or peralkylammonium groups and/or hydroxy groups and/or polyether groups having a suitable chain length, preferably having more than 10 alkylene oxide units. Preference is given to sulfonate salt, sulfonic acid, carboxylate salt, carboxylic acid, phosphonate salt and phosphonic acid groups.

Preferred classes of water-soluble ligands are phosphines, e.g. trialkylphosphines, tricycloalkylphosphines, triarylphosphines, dialkylarylphosphines, alkyldiarylphosphines and heteroarylphosphines such as tripyridylphosphine and trifurylphosphine, where the three substituents on the phosphorus can be identical or different and chiral or achiral and where one or more of the substituents can link the phosphorus groups of a plurality of phosphines and where part of this linkage can also be one or more metal atoms, phosphites, phosphinous esters and phosphonous esters, phosphols and dibenzophosphols, including cyclic, oligocyclic and polycyclic compounds containing phosphorus atoms, substituted by the above groups.

Further suitable groups of water-soluble complexing ligands include, for example, bipyridines, phenanthrolines, porphyrins and alizarins which are modified by the above-mentioned groups.

Water-soluble phosphines which are preferably used are water-soluble triarylphosphines which can contain, apart from the substituents which make them water soluble, F, alkyl or alkoxy groups preferably having 1–12 carbon atoms, and also those of the formulae (II) to (VIII).

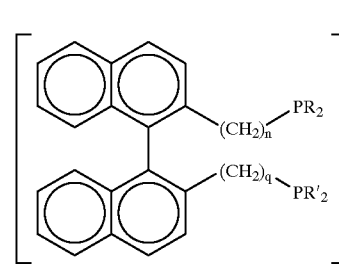

(II)

which are substituted 1 to 8 times with
$SO_3^-M^+$, $PO_3^{2-}2M^+$, $CO_2^-M^+$
$NR_4^+X^-$, $PR_4^+X^-$, OH

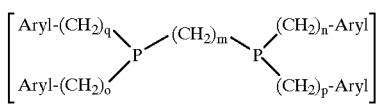 (III)

which are substituted 1 to 8 times with
$SO_3^-M^+$, $PO_3^{2-}2M^+$, $CO_2^-M^+$
$NR_4^+X^-$, $PR_4^+X^-$, OH

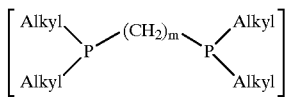 (IV)

which are substituted 1 to 8 times with
$SO_3^-M^+$, $PO_3^{2-}2M^+$, $CO_2^-M^+$
$NR_4^+X^-$, $PR_4^+X^-$, OH $[P((CH_2)_n\text{-Aryl})_{3-s}(\text{Alkyl})_s]$ (V)

which are substituted 1 to 8 times with
$SO_3^-M^+$, $PO_3^{2-}2M^+$, $CO_2^-M^+$
$NR_4^+X^-$, $PR_4^+X^-$, OH

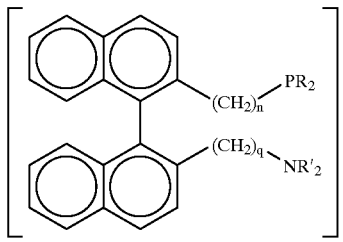 (VI)

which are substituted 1 to 8 times with
$SO_3^-M^+$, $PO_3^{2-}2M^+$, $CO_2^-M^+$
$NR_4^+X^-$, $PR_4^+X^-$, OH

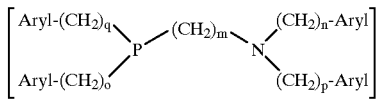 (VII)

which are substituted 1 to 8 times with
$SO_3^-M^+$, $PO_3^{2-}2M^+$, $CO_2^-M^+$
$NR_4^+X^-$, $PR_4^+X^-$, OH

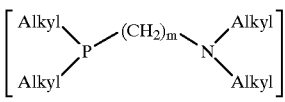 (VIII)

which are substituted 1 to 8 times with
$SO_3^-M^+$, $PO_3^{2-}2M^+$, $CO_2^-M^+$
$NR_4^+X^-$, $PR_4^+X^-$, OH where the symbols and indices having the following meanings:

Aryl: a phenyl or naphthyl group which may also bear one or more substituents R;

Alkyl: a straight-chain or branched alkyl group having from 1 to 8 carbon atoms;

R, R': F or preferably alkyl, aryl or aralkyl having from 1 to 18 carbon atoms;

M: alkali metal, alkaline earth metal or $NR_4$;

X: halogen, $BF_4$, $PF_6$, $OSO_2CF_3$, $\frac{1}{2}[SO_4]$;

l, m: 1 to 8;

n, o, p, q: 0, 1 to 8;

s: 0, 1 to 3.

Examples of particularly preferred water-soluble complexing ligands are shown below:

(unless otherwise indicated, R is as defined for the formulae (II) to (VIII))

1. Sulfonated phosphines

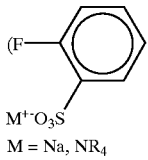

$[(C_6H_5)(CH_2)_n]_3P$  n = 1, 2, 3 and 6
  |
  $SO_3^-M^+$   p- and/or o-sulfonated

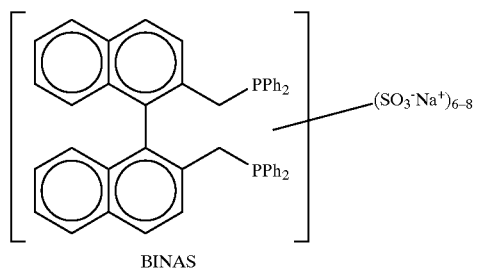

BINAS

-continued

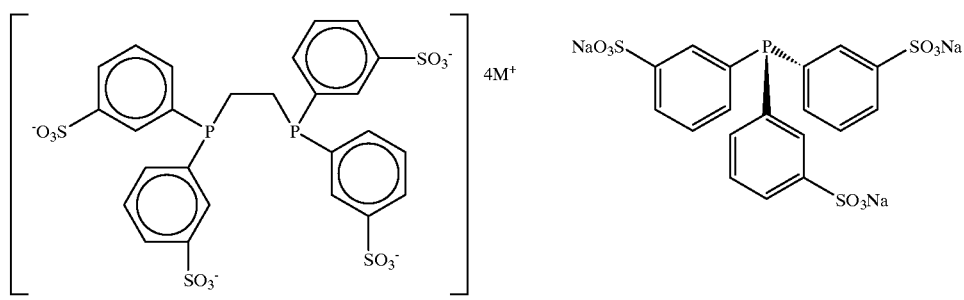

M = Na⁺, NR₄⁺

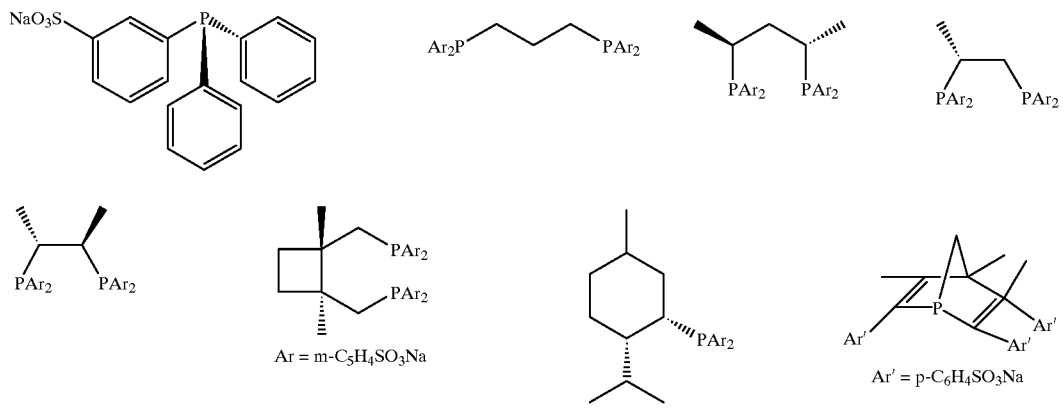

$R_{3-n}P(p-C_6H_4SO_3K)_n$  R = $C_6H_5$, 2-pyridyl, 3-pyridyl; n = 1–3
$P[p-OC_6H_4SO_3(NH(i-octyl)_3]_3$ 2. Phosphines having hydrophilic groups in the periphery

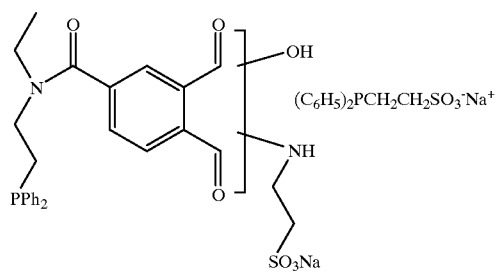

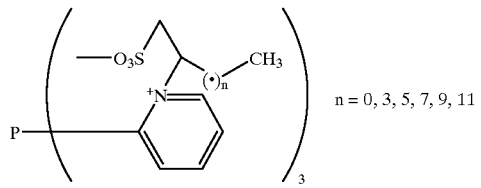

3. Phosphines having quaternized aminoalkly and aminoaryl substituents

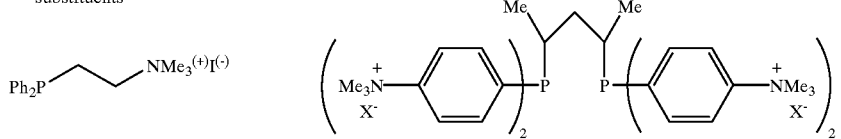

$Ph_2P$—U—$NHR_2^+X^-$  $Ph_2P$—U—$NR_3^+X^-$  U = —$CH_2CH_2$—, —$CH(CH_3)CH_2$—, —$CH_2CH(CH_3)CH_2$—;
R = $CH_3$;

$X = I^\ominus, Br^\ominus, Cl^\ominus, OSO_2CF_3^\ominus, BF_4^\ominus, PF_6^\ominus$ -continued 4. Carboxylated phosphines

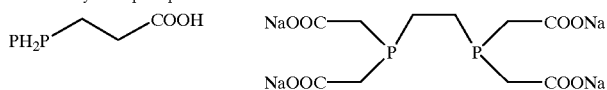 

o, m, p- substituted

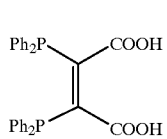 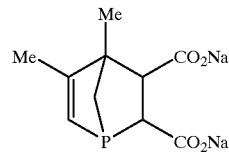

5. Phosphines having hydroxyalkyl or polyether substituents

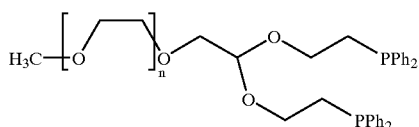 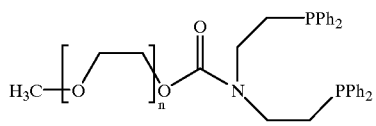

n > 16      n = 12, 16, 110

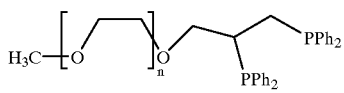 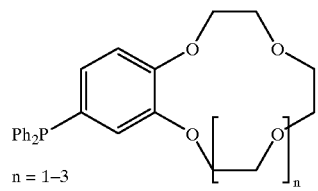

n = 1–8      n = 1–3

6. Phosphinoalkylphosphonium salts

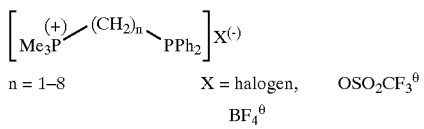

n = 1–8     X = halogen, $OSO_2CF_3^{\ominus}$, $BF_4^{\ominus}$

7. Phosphites

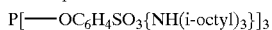

P[—$OC_6H_4SO_3\{NH(i\text{-octyl})_3\}$]$_3$

Very particularly preferred water-soluble phosphine ligands are:

TPPTS

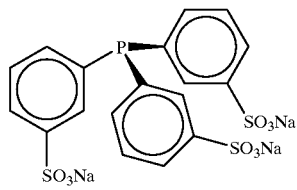

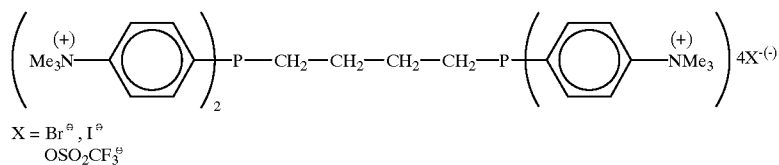

X = $Br^{\ominus}$, $I^{\ominus}$, $OSO_2CF_3^{\ominus}$

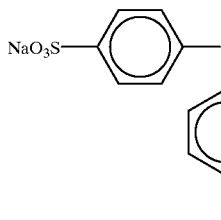
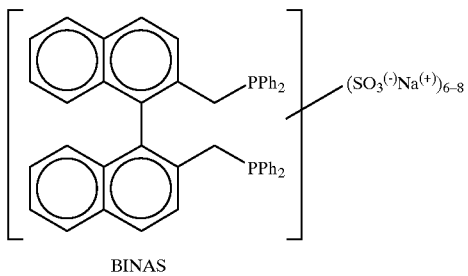

BINAS

In the formula (I)
Y is preferably H, CO, CN or halogen, preferably Cl, or an alkali metal or alkaline earth metal ion, preferably Na, K or Li.

If M is palladium, Y is particularly preferably $Cl^{\ominus}$, CO, Na, K, Li.

If M is rhodium, Y is particularly preferably $Cl^{\ominus}$, CO, Na, K, Li, H.

The majority of the water-soluble complexing ligands used according to the invention are known from the literature. The syntheses of these compounds are described, for example, in W. A. Herrmann and C. W. Kohlpainter, Angew. Chem. Int. Ed. Engl. 32 (1993) 1524 and the literature cited therein or can be carried out by literature methods or analogous methods with which those skilled in the art are familiar. The preparation of BINAS is described in EP-A 0 571 819 or U.S. Pat. No. 5,347,9045. If desired, mixtures of two or more different water-soluble ligands can also be used.

The water-soluble metal catalyst of the formula (I) can be synthesized separately or else be prepared in situ by combining a ruthenium, nickel, palladium or rhodium salt, e.g. rhodium chloride hydrate, ruthenium chloride, a nickel halide or a palladium(II) salt, with a water-soluble ligand.

If desired, a reducing agent is added. In general, hydrogen is the appropriate reducing agent for preparing the active catalyst species.

Some of the metal complexes of the formula (I) used according to the invention are known from the literature (see, for example, EP-A-0 372 313 or J. Organomet. Chem. 1990, 389, 103).

Particularly preferred metal complexes of the formula (I) are $Rh(CO)Cl(TPPTS)_2$, where TPPTS is triphenylphosphinetrisulfonic acid trisodium salt, $Pd(TPPTS)_2$ and $Ru(TPPTS)_2Cl_2$.

The invention further provides a process for preparing $Rh(CO)Cl(TPPTS)_2$. Said catalyst can be easily obtained by a novel process from an aqueous solution of TPPTS and rhodium trichloride and subsequent addition of formaldehyde followed by heating, as is described below in Example 1. This process is significantly simpler than that described in EP-0 372 313. Isolation and chromatographic purification of the intermediates is unnecessary. The TPPTS can be used as technical-grade product as is obtained in production. The carbon monoxide is replaced by the aqueous formaldehyde solution, so that handling in terms of apparatus is also significantly simplified here.

The process of the invention is advantageously carried out in an autoclave. Autoclaves are, according to Römpps Chemie Lexikon, closable metal vessels which are tested to a high superatmospheric pressure and have a tightly closed lid which is screwed on and secured by means of a bayonet lock or is pressed on. This autoclave head has, for example, connections for a bursting disk or a safety valve, manometer, thermometer and often also a stirring apparatus which is installed so as to be gastight. Apart from stationary autoclaves with internal stirring (also magnetic stirring) there are also shaking autoclaves and rotating autoclaves. In the case of laboratory autoclaves (capacity from about 100 ml to a number of liters), the autoclave is usually heated electrically; larger autoclaves in industrial process engineering (up to a number of $m^3$) are usually heated by means of steam. Autoclaves in which reactions occur with the consumption of gases, e.g. pressure hydrogenation, also have an inlet for the gas-containing starting material which is usually conveyed by a compressor. In most cases, the autoclaves are constructed of high-alloy steel (e.g. V4A), although there are also special autoclaves made of copper, light metal and Monel metal.

The catalyst comprising a metal complex of the formula (I) is preferably used in aqueous solution, with the amount of water being able to be within a wide range. Since the reaction takes place in the aqueous phase, more nitroaromatic will dissolve in the water, thus accelerating the reduction, if relatively large amounts of water are provided. The amount of water thus has, within certain limits, an influence on the reaction rate. Since the catalyst itself is extremely readily soluble in water, this does not restrict the amount of water. In addition, account must be taken of the fact that water is formed in the reduction itself. For one mole of substrate and one millimole of catalyst, use is generally made of 10–1000 ml, preferably 50–500 ml, in particular 100–200 ml, of water. The molar ratio of the catalyst to substrate is generally from 1:100 to 1:100,000, preferably from 1:500 to 1:10,000, in particular from 1:500 to 1:5000. The ratios of catalyst to substrate and catalyst to water give a ratio of catalyst to water of from about 1:500 to 1:200,000, preferably from 1:2000 to 1:190,000, in particular from 1:5000 to 1:100,000.

If the water-soluble catalyst used is $Rh(CO)Cl(TPPTS)_2$, the ratio of substrate to catalyst is, in particular, from 1:2000 to 1:5000.

The respective reaction rate depends on many parameters such as pressure, temperature, the amount of catalyst, the amount of substrate and the amount of water. However, it also depends critically on the solubility of the substrate in water. Nitroaromatics which contain, for example, an ethoxy or methoxy group are generally more readily water-soluble than alkylated compounds. The reaction time is usually, depending on the reaction conditions and the nature of the nitroaromatic, from 30 minutes to 10 hours. The hydrogen uptake generally stops sharply when the reduction is complete.

The reaction temperature is generally from 20 to 150° C., preferably 50–130° C., in particular from 60 to 110° C. The hydrogen pressure can be 1–150 bar, preferably 10–100 bar, particularly preferably 10–20 bar. Frequently selected reaction conditions are 100° C. and 20 bar hydrogen pressure. If the water-soluble catalyst used is Rh(CO)Cl(TPPTS)$_2$, the preferred reaction temperature is from 70 to 130° C., in particular from 90 to 110° C.

After the reduction is complete, the reaction product is separated from the aqueous catalyst solution. The aqueous catalyst solution can be used for further reductions. No loss in activity is observed on recycling. When the catalyst is recycled a plurality of times, the aqueous catalyst solution is increasingly diluted by the water of reaction formed. The original concentration ratios can be restored, for example, by means of membrane filters or by evaporation under reduced pressure.

The catalyst system is relatively insensitive to air, but the aqueous solution should nevertheless be handled under inert conditions so as to ensure as long as possible a life and recyclability of the catalyst.

In the reduction, it is not necessary to add an organic solvent for the nitroaromatic. The complicated and costly work-up of the solvent is thus also avoided. In addition, the filtration from the catalyst necessary in the heterogeneously catalyzed reduction is not needed either. However, it is also possible to dilute the nitro compound with an organic solvent, for example with toluene, o-xylene, m-xylene, p-xylene, mixtures of isomeric xylenes, ethylbenzene, mesitylene, chlorobenzene, dichlorobenzene, chlorotoluene, cyclohexane, cumene, decalin, ethyl acetate, butyl acetate or a mixture of two or more of these solvents.

Preferred starting materials for the process of the invention are aromatic nitro compounds. Particularly preferred starting compounds are those of the formula (IX)

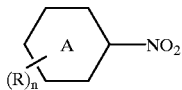

(IX)

where the symbols and indices have the following meanings:

is an aromatic hydrocarbon which may also contain heteroatoms, preferably —O— and/or —N— and/or —S— and has from 4 to 20 carbon atoms, preferably phenyl or naphthyl;

n is, depending on the parent aromatic unit, 0, 1, 2, 3, 4 or 0, 1, 2, 3, 4, 5, 6, preferably 0, 1 or 2;

R are identical or different and are each —H, —F, —Cl, —Br, —I, CN, —SCN, —OCN, —OH, —NH$_2$, —CHO, —NO$_2$, —SO$_3$H, R', OR', —COOR', —OCOR', —NHR', —NR'$_2$, NHCOR';

R' are identical or different and are each H, a branched or unbranched alkyl, alkenyl or alkynyl group having 1 or from 2 to 12, preferably 1 or from 2 to 8, carbon atoms in which one or more CH$_2$ groups may be replaced by —O— and/or one or more H atoms may be replaced by —F, —Cl, —Br, —I, —OH and/or —NH$_2$; or an aromatic hydrocarbon radical which may also contain heteroatoms, preferably —O—, —N— and/or —S—, and which may also bear further substituents R, and has from 4 to 20 carbon atoms, preferably phenyl or naphthyl.

Preference is given to compounds of the formula (IX) in which n is 0, 1 or 2 and R is a methyl, ethyl, n-propyl, isopropyl, n-butyl, tert-butyl, n-pentyl, i-pentyl, n-hexyl, n-heptyl, n-octyl, 2-ethylhexyl, 2-ethyldecyl, n-decyl or n-dodecyl group, furthermore a methoxy, ethoxy, propoxy, isopropoxy, butoxy, pentyloxy, hexyloxy, octyloxy, hydroxy, 2-ethylhexyloxy, decyloxy or dodecyloxy group, furthermore a carboxylic acid, carboxylic acid methyl ester, carboxylic acid ethyl ester, carboxylic acid propyl ester, carboxylic acid butyl ester, carboxylic acid pentyl ester, carboxylic acid hexyl ester, carboxylic acid 2-ethylhexyl ester, carboxylic acid phenyl ester, formyl, carboxamide, N,N-dimethylcarboxamide, N,N-diethylcarboxamide, N-methylcarboxamide or N-ethylcarboxamide group, furthermore an N,N-dimethylamino, N,N-diethylamino, N-methylamino, N-ethylamino, N,N-methylethylamino, N,N-dipropylamino, N,N-dibutylamino, N-morpholino group, an acetoxy, propionyloxy or butyryloxy group and/or a phenyl group which may likewise be substituted.

Very particularly preferred starting compounds are those of the formula (X)

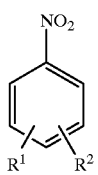

(X)

where R$^1$ and R$^2$ can be identical or different and are hydrogen, C$_1$–C$_4$-alkyl, C$_1$–C$_4$-alkoxy, phenyl, C$_1$–C$_4$-alkylphenyl, nitro, amino, cyano, —COOR$^3$, —SO$_2$OR$^3$ or sulfamoyl and R$^3$ is hydrogen or the equivalent of a cation.

Accordingly, particularly preferred products of the process of the invention are amino compounds of the formula (XI),

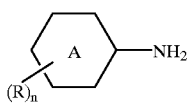

(XI)

where the symbols and indices are as defined for formula (IX).

The compounds prepared according to the invention have a wide variety of uses, for example as intermediates for preparing active compounds, polymers and dyes.

The compounds prepared according to the invention preferably serve as starting materials for preparing diazonium salts and benzoxazoles, for example fenoxaprop-P-ethyl, a selective herbicide which is marketed under the name Puma® by AgrEvo, Frankfurt, Germany.

Diazonium salts serve, for example, as intermediates for preparing active compounds, polymers and dyes and in particular as diazo copying precursors.

The documents cited in the description, which, for example, illustrate the technical field of the invention or describe the preparation of compounds used according to the invention, are expressly incorporated by reference into this application.

The disclosure of the German Patent Applications 195 298 74.8 and 196 193 59.1, whose priority is claimed by the

EXAMPLE 1
Preparation of the catalyst Rh(CO)Cl(TPPTS)

RhCl$_3$xH$_2$O (0.26 g, 1 mmol) was added to a boiling solution of TPPTS (29.2% strength, 19.5 g, 10 mmol). After about 15–20 seconds, a formaldehyde solution (35% strength, 15 g, 175 mmol) was added. The solution changed color from dark red to yellow. It was subsequently heated at about 80° C. for 10 minutes and ethanol was added dropwise until a slight turbidity appeared. On cooling, TPPTS and the Rh-TPPTS complex crystallized from the solution. The crystals of the complex were largely freed of excess TPPTS by washing with ethanol/H$_2$O 80/20. Recrystallization from ethanol/H$_2$O and drying under reduced pressue gave the complex in highly enriched form.

EXAMPLE 2
Reduction of nitrobenzene

In a 2 l autoclave fitted with gas-introduction stirrer, a two-phase system comprising 200 g (1.62 mol) of nitrobenzene, 200 g of water and 0.31 g (0.235 mmol) of Rh(CO)Cl(TPPTS)$_2$ was hydrogenated at 20 bar and 100° C. After 8 hours, the aniline content was 87.1% at a conversion of 99.3%. The aqueous catalyst solution was separated off in a separating funnel.

EXAMPLE 3
Reduction of nitrobenzene using recycled catalyst 200 g of nitrobenzene were reduced under the reaction conditions indicated in Example 2 in the presence of the catalyst solution recovered from that example. This time, a conversion of 98% was obtained after 3.5 hours. The aniline content was 95.5%.

EXAMPLE 4
Reduction of 2-chloronitrobenzene using recycled catalyst 200 g (1.27 mol) of 2-chloronitrobenzene were reacted under identical reaction conditions to Example 2 using the catalyst recovered from Example 2. After 8.5 hours, a solution having the following composition was obtained: 11.0% of aniline (by reductive dehalogenation), 81.8% of 2-chloroaniline and 3.2% of unreacted 2-chloronitrobenzene.

EXAMPLE 5
Reduction of 4-ethoxynitrobenzene 200 g (1.31 mol) of 4-ethoxynitrobenzene in 400 g of toluene were reacted under identical reaction conditions to Example 2 using fresh rhodium catalyst from Example 1 (0.23 mol in 200 ml of water). The reaction was complete after one hour. According to GC, the solution after phase separation contained 95.5% of 4-ethoxyaniline and 1.4% of 4-ethoxynitrobenzene.

EXAMPLE 6
Reduction of 3-nitrotoluene using recycled catalyst

Using the aqueous catalyst solution recovered from Example 5, 200 g (1.87 mol) of 3-nitrotoluene in 400 g of toluene were reduced under identical reaction conditions. After 3 hours 40 minutes, the compound was completely converted into 3-methylaniline. Starting material could no longer be detected in the solution.

EXAMPLE 7
Reduction of 2,4-dimethylnitrobenzene using recycled catalyst

A mixture of 200 g (0.76 mol) of 2,4-dimethylnitrobenzene and recycled catalyst solution was heated at 100° C. for 10 hours under a hydrogen pressure of 20 bar. GC analysis of the product solution indicated a 3,4-dimethylaniline content of 97.7%.

EXAMPLE 8
Reduction of 5-chloro-2-nitrophenol

In a 2 l autoclave, 100 g (0.576 mol) of 5-chloro-2-nitrophenol were suspended in 200 ml of water and hydrogenated at 100° C./20 bar of hydrogen. A catalyst solution comprising 0.129 g (0.576 mmol) of Pd(ac)$_2$, 2 ml of DMSO and 3.9 ml of TPPTS/H$_2$O solution (0.6 molar) was added at the beginning of the reaction. After 7 hours, the conversion was 99.3% and the solution had a 5-chloro-2-aminophenol content of 95.53%. The catalyst phase was separated off by filtration of the product and reused.

EXAMPLE 9
Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen. The catalyst solution from Example 8 was added at the beginning of the reaction. After 10 hours, the conversion was 99.8% and the solution had a 5-chloro-2-aminophenol content of 96.5%. The catalyst phase was separated off by filtration of the product and reused.

EXAMPLE 10
Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen. The catalyst solution from Example 9 was added at the beginning of the reaction. After 5.5 hours, the conversion was 99.9% and the solution had a 5-chloro-2-aminophenol content of 95.1%. The catalyst phase was separated off by filtration of the product and reused.

EXAMPLE 11
Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen. The catalyst solution from Example 10 was added at the beginning of the reaction. After 9.5 hours, the conversion was 99.9% and the solution had a 5-chloro-2-aminophenol content of 95.6%. The catalyst phase was separated off by filtration of the product.

EXAMPLE 12
Reduction of 5-chloro-2-nitrophenol

In a 2 l autoclave, 100 g (0.576 mol) of 5-chloro-2-nitrophenol were suspended in 200 ml of water and hydrogenated at 100° C./20 bar of hydrogen at pH 7.5. A catalyst solution comprising 0.129 g (0.576 mmol) of Pd(ac)$_2$, 2 ml of DMSO and 3.9 ml of TPPTS/H$_2$O solution (0.6 molar) was added at the beginning of the reaction. After 2.5 hours, the conversion was 99.8% and the solution had a 5-chloro-2-aminophenol content of 82.4%. The catalyst phase was separated off by filtration of the product and reused.

EXAMPLE 13
Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen at pH 7.5. The catalyst solution from Example 12 is present application, and the Abstract of this application are hereby expressly incorporated by reference into this application:

The invention is illustrated by the examples, without being restricted thereby.

added at the beginning of the reaction. After 6.5 hours, the conversion was 99.6% and the solution had a 5-chloro-2-aminophenol content of 92.8%. The catalyst phase was separated off by filtration of the product.

EXAMPLE 14

Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen at pH 7.5. The catalyst solution from Example 13 was added at the beginning of the reaction. After 8.5 hours, the conversion was 99.6% and the solution had a 5-chloro-2-aminophenol content of 95.2%. The catalyst phase was separated off by filtration of the product.

EXAMPLE 15

Reduction of 5-chloro-2-nitrophenol using recycled catalyst

In a 2 l autoclave, 100 g (0.576 mol) of 5-chloro-2-nitrophenol were hydrogenated at 100° C./20 bar of hydrogen at pH 7.5. The catalyst solution from Example 14 was added at the beginning of the reaction. After 9.5 hours, the conversion was 99.9% and the solution had a 5-chloro-2-aminophenol content of 94.3%. The catalyst phase was separated off by filtration of the product.

EXAMPLE 16

Reduction of 5-chloro-2-nitrophenol

In a 2 l autoclave, 100 g (0.576 mol) of 5-chloro-2-nitrophenol were suspended in 200 ml of water and hydrogenated at 100° C./20 bar of hydrogen. A catalyst solution comprising (0.576 mmol) of Ru(TPPTS)$_3$Cl$_2$ was added at the beginning of the reaction. After 2.5 hours, the conversion was 99.8% and the solution had a 5-chloro-2-aminophenol content of 92.4%. The catalyst phase was separated off by filtration of the product and reused.

We claim:

1. A process for reducing nitro groups to amino groups, which comprises:

providing a nitro compound from the formula:

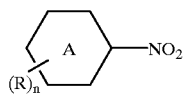

(IX)

where:

is an aromatic hydrocarbon, said aromatic hydrocarbon having from 6 to 20 carbon atoms;

n is 0, 1, 2, 3, 4, or 5;

R are identical or different and are each —H, —F, —Cl, —Br, —I, —CN, —SCN, —OCN, —OH, —NH$_2$, —CHO, —NO$_2$, —SO$_3$H, —R', —OR', —COOR', —OCOR', —NHR', —NR'$_2$, —NHCOR';

R' are identical or different and are each H, a branched or unbranched alkyl, alkenyl, or alkynyl group having 1 or from 2 to 12 carbon atoms in which one or more CH$_2$ groups may be replaced by —O— and/or one or more H atoms may be replaced by —F, —Cl, —Br, —I, —OH and/or —NH$_2$; or an aromatic hydrocarbon radical and combinations thereof; and which may also include substituents R, and has from 6 to 20 carbon atoms;

reacting said nitro compound with hydrogen in the presence of a water-soluble metal catalyst of the formula (I)

$$M(L)_n(Y)_m \qquad (I)$$

where the symbols and indices have the following meanings:

M is ruthenium, rhodium, nickel or palladium;

L are identical or different and are each a water-soluble ligand selected from the group of: phosphines, phosphites, phosphinous esters, phosphonous esters, phospholes, bipyridines, phenanthrolines, porphyrins and alizarins;

Y are identical or different and are selected from the group of: H, CO, CN or a halogen, or an alkali metal ion or an alkaline earth metal ion;

n is 1, 2, 3 or 4:

m is 0, 1 or 2.

2. The process as claimed in claim 1, wherein the water-soluble ligand L is substituted with at least one substituent selected from the following group: sulfonic acids, sulfonate salts, carboxylic acids, carboxylate salts, phosphonic acids, phosphonate salts, phosphonium salts, phosphinic acids, phosphinate salts, peralkylammonium groups, hydroxy groups and polyether groups.

3. The process as claimed in claim 1, wherein a molar ratio of catalyst: substrate of from 1:100 to 1:100,000 is selected.

4. The process as claimed in claim 1, wherein the water-soluble ligand is a water-soluble triarylphosphine which can contain, apart from the substituents which make it water-soluble, further substituents, or a water-soluble phosphine of the formulae (II) to (VIII):

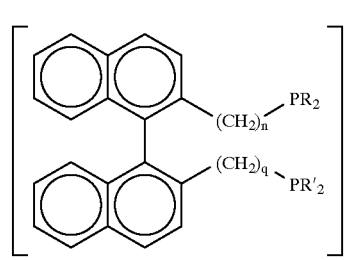

(II)

which are substituted 1 to 8 times with
SO$_3^-$M$^+$, PO$_3^{2-}$2M$^+$, CO$_2^-$M$^+$
NR$_4^+$X$^-$, PR$_4^+$X$^-$, OH

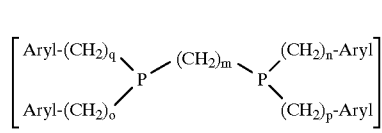

(III)

which are substituted 1 to 8 times with
SO$_3^-$M$^+$, PO$_3^{2-}$2M$^+$, CO$_2^-$M$^+$
NR$_4^+$X$^-$, PR$_4^+$X$^-$, OH -continued

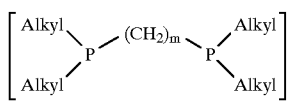   (IV)

which are substituted 1 to 8 times with
$SO_3^-M^+$, $PO_3^{2-}2M^+$, $CO_2^-M^+$
$NR_4^+X^-$, $PR_4^+X^-$, OH $[P((CH_2)_n\text{-Aryl})_{3-s}(\text{Alkyl})_s]$   (V)

which are substituted 1 to 8 times with
$SO_3^-M^+$, $PO_3^{2-}2M^+$, $CO_2^-M^+$
$NR_4^+X^-$, $PR_4^+X^-$, OH

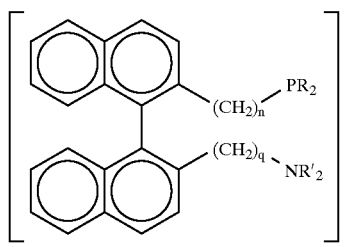   (VI)

which are substituted 1 to 8 times with
$SO_3^-M^+$, $PO_3^{2-}2M^+$, $CO_2^-M^+$
$NR_4^+X^-$, $PR_4^+X^-$, OH

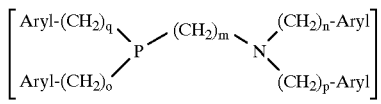   (VII)

which are substituted 1 to 8 times with
$SO_3^-M^+$, $PO_3^{2-}2M^+$, $CO_2^-M^+$
$NR_4^+X^-$, $PR_4^+X^-$, OH

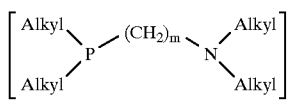   (VIII)

which are substituted 1 to 8 times with
$SO_3^-M^+$, $PO_3^{2-}2M^+$, $CO_2^-M^+$
$NR_4^+X^-$, $PR_4^+X^-$, OH where the symbols and indices having the following meanings:

Aryl: a phenyl or naphthyl group which may also bear one or more substituents R;

Alkyl: a straight-chain or branched alkyl group having from 1 to 8 carbon atoms:

R, R': alkyl, aryl or aralkyl having from 1 to 18 carbon atoms;

M: alkali metal, alkaline earth metal or $NR_4$;

X: halogen, $BF_4$, $PF_6$, $OSO_2CF_3$, $\frac{1}{2}(SO_4)$;

m: 1 to 8;

n, o, p, q: 0, 1 to 8;

s: 0, 1 to 3.

5. The process as claimed in claim 1, wherein the reaction temperature employed is from 20 to 150° C.

6. The process as claimed in claim 1, wherein the hydrogen pressure employed is from 1 to 150 bar.

7. The process as claimed in claim 1, wherein the nitro compound is diluted with an organic solvent selected from the group consisting of toluene, o-xylene, m-xylene, p-xylene, mixtures of isomeric xylenes, ethylbenzene, mesitylene, chlorobenzene, dichlorobenzene, chlorotoluene, cyclohexane, cumene, decalin, ethyl acetate, butyl acetate or a mixture of two or more of these solvents.

8. The process as claimed in claim 1, wherein:

is an aromatic hydrocarbon selected from phenyl or naphthyl; and n is 0, 1, 2, 3, 4.

9. The process as claimed in claim 1, wherein n is 0, 1 or 2.

10. The process as claimed in claim 1, wherein:
said nitro compound has a formula:

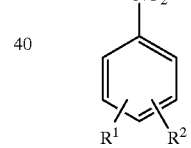   (X)

where $R^1$ and $R^2$ can be identical or different and are selected from the group of: hydrogen, $C_1$–$C_4$-alkyl, $C_1$–$C_4$-alkoxy, phenyl, $C_1$–$C_4$-alkylphenyl, nitro, amino, cyano, —$COOR^3$, —$SO_2OR^3$ or sulfamoyl and $R^3$ is hydrogen.

* * * * *